United States Patent [19]
Lammers

[11] Patent Number: 5,934,279
[45] Date of Patent: Aug. 10, 1999

[54] PESSARY INSERTION APPARATUS

[76] Inventor: Delmar R. Lammers, 117 April Waters North, Montgomery, Tex. 77356

[21] Appl. No.: 08/985,106

[22] Filed: Dec. 4, 1997

Related U.S. Application Data

[60] Provisional application No. 60/032,104, Dec. 4, 1996.

[51] Int. Cl.$^6$ ........................................................ A61F 6/06
[52] U.S. Cl. ............................................ 128/830; 128/836
[58] Field of Search ...................................... 128/830–841

[56] References Cited

U.S. PATENT DOCUMENTS

| | | |
|---|---|---|
| 1,857,127 | 5/1932 | Eggert . |
| 2,104,275 | 1/1938 | Schleicher . |
| 2,146,574 | 2/1939 | Hay . |
| 2,338,135 | 1/1944 | Schmitz . |
| 2,446,724 | 8/1948 | Schmitz, Jr. . |
| 2,452,229 | 10/1948 | Bray et al. . |
| 2,830,582 | 4/1958 | Ljung . |
| 3,635,215 | 1/1972 | Shea et al. . |
| 4,742,820 | 5/1988 | Leuchtenberger ........................ 128/838 |
| 4,858,624 | 8/1989 | Shihata ..................................... 128/838 |
| 4,993,432 | 2/1991 | Shields et al. ............................ 128/838 |

FOREIGN PATENT DOCUMENTS

| | | | |
|---|---|---|---|
| 0138245 | 1/1903 | Germany ................................ | 128/838 |

OTHER PUBLICATIONS

Flyer: Bioteque America, Inc., Pessary Flexible Silicone Ring Rings Are The Most Commonly Used Pessaries For Minor Degree Prolapse (Date Unknown).

*Primary Examiner*—Michael A. Brown
*Attorney, Agent, or Firm*—Jeffrey E. Griffin

[57] ABSTRACT

A pessary insertion apparatus providing a rigid, elongated body having an crescentic shape. The body defines a bottom portion and a pair of opposing side wall portions. The side wall portions extending from the bottom portion a distance approximately equal to or greater than the height of the folded pessary. The body sized and adapted to hold the pessary therein. The crescentic shape extending the full length of the body so that, when in the vaginal cavity, the body holds the vaginal cavity open and defines a passageway through which the user may reach the back end of the pessary to force the pessary from the body and into position. Holes in the bottom portion of the body enhance gripping of the pessary insertion apparatus.

15 Claims, 2 Drawing Sheets

PESSARY INSERTION APPARATUS

This application claims the benefit of U.S. Provisional Application Ser. No. 60/032,104 filed Dec. 4, 1996.

BACKGROUND OF THE INVENTION

1. Field of the Invention

The present invention relates to the field of pessary introducers. More specifically, the invention relates to a pessary insertion apparatus adapted to hold a pessary in a folded position and to provide an open and accessible passageway for a finger to access the rearward end of the pessary and force the pessary from the pessary insertion apparatus and into the proper position.

Many women suffer from prolapse of the vagina or other body parts in the area of the vagina. Often these women are required to use a ring type (or other) pessary to support the organs to prevent excess falling or slipping. A ring type pessary is inserted into the vaginal cavity. Typically, the pessary is constructed of a resilient, though fairly rigid, silicone that permits the pessary to be folded for insertion. Generally, the pessary is inserted using the hands of the patient or the doctor. It is folded with the leading edge of the formed crescent pointing downward. The pessary is then inserted through the vagina into the posterior fornix and unfolds after passing the introitus. Once inserted, the pessary may be rotated to ensure that it is fully unfolded and properly positioned. Insertion of the pessary is typically a painful process.

The pessary must be removed periodically for cleaning and during certain activities, such as intercourse, x-rays, ultrasound, or MRI. Therefore, insertion of the pessary is a periodic activity that the patient must endure repeatedly.

Besides being painful, insertion of the pessary is also very difficult for the patient or the doctor. To enhance insertion into the vaginal cavity and comfort during insertion, the pessary is typically coated with a lubricant which makes the pessary relatively slippery and difficult to handle. Then, the lubricated, resilient pessary must be held in a folded position while being placed in the confined area of the vaginal cavity. These conditions make insertion of the pessary difficult for a doctor or other person, such as a family member of the patient, skilled in inserting pessaries, but makes insertion by the patient extremely difficult.

Accordingly, there is a need for a device to help a patient and others insert a pessary that makes the pessary easier to handle and provides as much comfort as possible.

2. Related Art.

Some prior efforts have attempted to address the problem of pessary introduction and the related problem of diaphragm introduction by providing a device that holds the pessary in a folded position and provides an elongated handle to facilitate introduction. However, none of the prior efforts are adapted to hold a pessary in a folded position and define a passageway therethrough that provides the user's finger access to the pessary so that the user may easily push the pessary from the device for proper positioning and ease of insertion. Additionally, none of the prior efforts allow the pessary to be folded with the leading edge of the formed crescent pointing downward, as is preferred in inserting a pessary, while providing a clear, unimpeded view of the pessary during insertion.

Thus, despite the use of the prior art features, there remains a need for a pessary insertion apparatus that will hold the pessary in the proper position for insertion and will define an open passageway that provides access to the pessary for removal from the device.

SUMMARY OF THE INVENTION

Accordingly, the objectives of the present invention are to provide, inter alia, a pessary insertion apparatus that:

facilitates insertion of a pessary;

holds a pessary in a folded position with the leading edge of the formed crescent pointing downward while allowing the user to clearly view the pessary during insertion.

defines a passageway through which the user may easily access the pessary and push the pessary from the pessary insertion apparatus;

provides ease of use; and is low in cost.

Other objects of the invention will become apparent from time to time throughout the specification and claims as hereinafter related.

To achieve such improvements, the present invention provides a pessary insertion apparatus adapted to facilitate the placement of a pessary in a vaginal cavity. The pessary insertion apparatus generally has a substantially rigid body having an arcuate shape that defines a trough and is adapted to receive and hold a pessary therein. The pessary insertion apparatus holds the pessary in the preferred folded position with the forward edge of the formed crescent pointing downward and with the fold proximal a bottom portion of the body. The body holds the vaginal cavity open and defines a passageway through which the user may reach the back end of the pessary to force the pessary from the pessary insertion apparatus.

In one aspect of the invention, the pessary insertion apparatus provides a substantially rigid body having an arcuate shape defining a bottom portion and a pair of opposing side wall portions and a trough therein. The body is sized and adapted to fit within the vaginal cavity. The side wall portions of the body extend from the bottom portion a distance approximately equal to or greater than the folded height of the pessary as measured from the bottom of the crescent formed by folding the pessary to the peripheral edge of the portion of the pessary held by the body. In this way, the body is sized and adapted to receive and hold a pessary in a folded position. The body is sized and adapted to receive and hold the pessary in a folded position with the fold formed by the folded pessary positioned proximal the bottom portion of the body so that the curve of the body and the curve of the pessary curve in the same direction. Preferably, the body is crescentic and elongated. The body is formed of a material that may be easily sterilized such as plastic or stainless steel. Preferably, the body has a front portion, adapted to receive and hold the pessary therein, and a rear end. The height of the side wall portions decrease from the front portion to the rear end so that the body may be more easily removed from the vaginal cavity.

In another aspect of the invention, the body is arcuate throughout its full length and the trough defines a passageway in the vaginal cavity through which a hand or finger of a user may reach a back end of the pessary so that the user may force the pessary from the body into position in the vaginal cavity.

A further aspect of the invention provides a pessary insertion apparatus having means for enhancing the grip on the body. One embodiment for the member for enhancing the grip is at least one hole defined by the body proximal a rear of the body which may alternatively be a plurality of holes. Additionally, the pessary insertion apparatus may include a handle attached to the rear of the body to enhance gripping of the pessary insertion apparatus.

Yet another aspect of the invention is a method of inserting a pessary into a vaginal cavity using a pessary insertion apparatus having a rigid, arcuate body. The method includes the steps of holding the pessary in a folded position in the front portion of the body, the curve of the folded pessary and the curve of the body curving in the same direction so that the fold created by the folded pessary lies proximal a bottom portion of the body, inserting the pessary, using the pessary insertion apparatus, into the vaginal cavity with the leading edge of the crescent formed by the folded pessary pointing downward to a position within the vaginal cavity where the pessary is to be inserted, holding the vaginal cavity open with the body to define a passageway through which a finger of the user may reach a back end of the pessary, pushing the pessary from the body into the position within the vaginal cavity where the pessary is to be inserted so that the pessary unfolds, and removing the pessary insertion apparatus from the vaginal cavity.

BRIEF DESCRIPTION OF THE DRAWINGS

The manner in which these objectives and other desirable characteristics can be obtained is explained in the following description and attached drawings in which.

Figure 1:
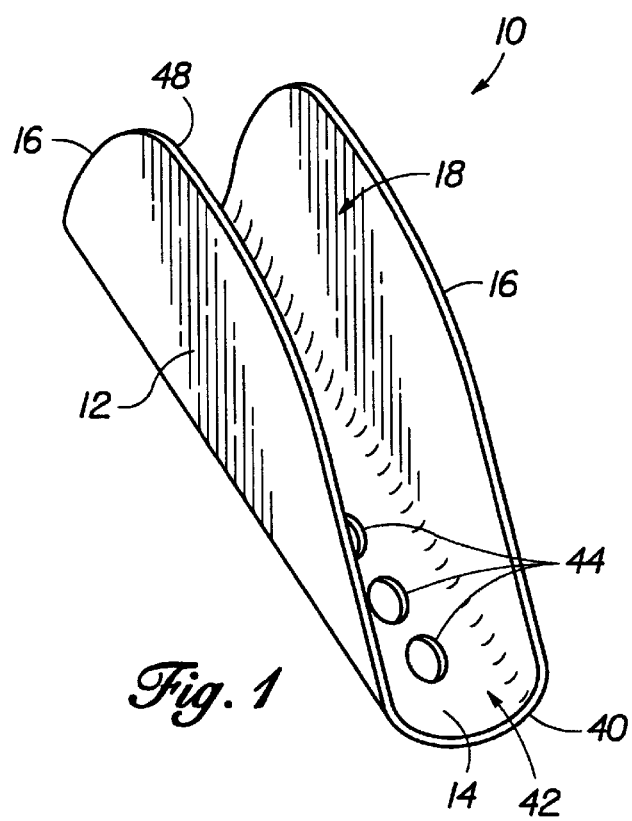
FIG. 1 is a perspective view of the pessary insertion apparatus.

It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

The present invention generally provides a pessary insertion apparatus 10 adapted to facilitate the placement of a pessary 20 in a vaginal cavity. The pessary insertion apparatus 10 generally has a substantially rigid body 12 having an arcuate shape that defines a trough 18 and is adapted to receive and hold a pessary 20 therein. The pessary insertion apparatus 10 holds the pessary 20 in the preferred folded position with the leading edge 24 of the formed crescent pointing downward and with the fold 22 proximal a bottom portion 14 of the body 12. The body 12 holds the vaginal cavity open and defines a passageway 42 through which the user may reach the back end 32 of the pessary 20 to force the pessary 20 from the pessary insertion apparatus 10.

As used herein, the term front or forward refers to that end of the pessary 20 or pessary insertion apparatus 10 that first enters the vaginal cavity when positioned therein. The term back or rear refer to the end opposite the front.

FIG. 1 is a perspective view of the pessary insertion apparatus 10. The pessary insertion apparatus 10 includes a body 12 formed of a material that may be easily sterilized, such as plastic or stainless steel. The surfaces of the body 12 are relatively smooth to facilitate comfort while sliding within the vaginal cavity and to facilitate the sliding therein. Further, the body 12 preferably minimizes sharp edges, such as those formed by corners, to further facilitate comfort and sliding. The body 12 is sized to fit within the vaginal cavity.

The body 12 has an arcuate shape that is preferably crescentic forming a body 12 wall that extends greater than 180°. The body 12 defines a bottom portion 14, a pair of opposing side wall portions 16, and a trough 18 therein. The side wall portions 16 extend up from the bottom portion 14 a distance that is approximately equal to or greater than the folded height of the portion of a pessary 20 held by the body 12.

Figure 2:
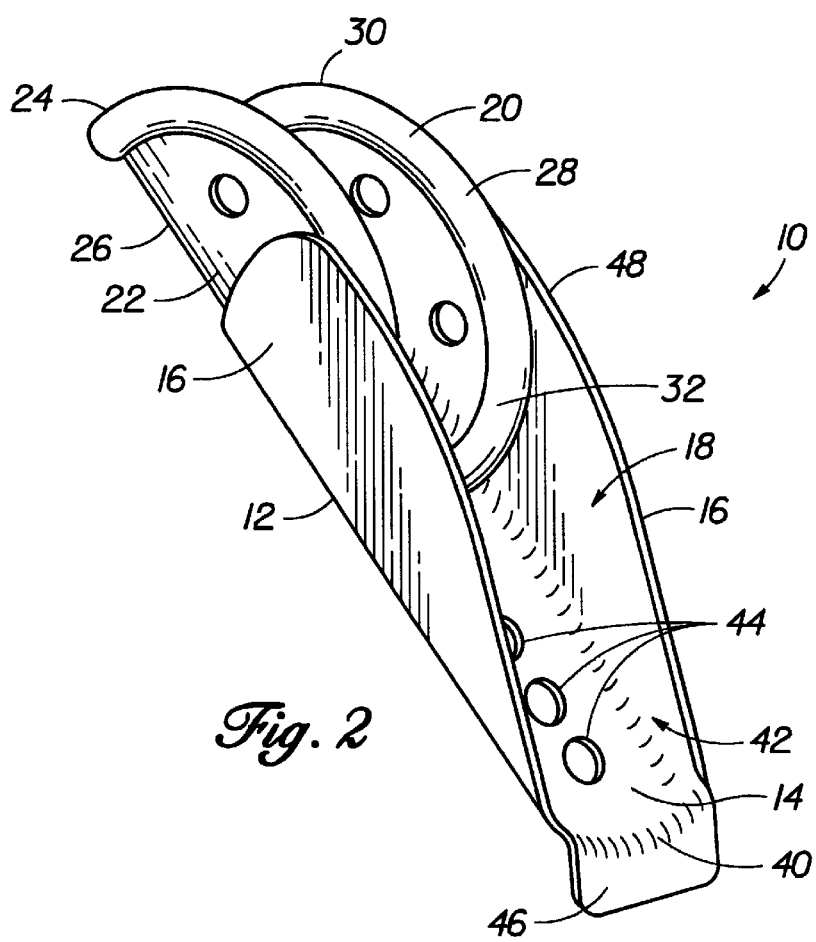
FIG. 2 is a perspective view of an alternative embodiment of the pessary insertion apparatus holding a pessary therein.

FIG. 2 shows an alternate embodiment of the pessary insertion apparatus 10 holding a folded pessary 20 therein. A pessary 20 is a circular or elongated ring having a support wall therein and is typically made from a resilient material, such as silicone, that allows the pessary 20 to be folded for insertion into the vaginal cavity and for unfolding once positioned within the vaginal cavity. Because the pessary 20 is intended to prevent further prolapse and support the body parts, the pessary 20 is relatively rigid and therefore exerts a relatively strong resilient force biasing the pessary 20 to an unfolded position. Accordingly, holding the pessary 20 in the folded position requires a relatively strong force. A pessary 20 adapted to prevent additional prolapse differs from a diaphragm designed to act as a contraceptive in that the diaphragm is much thinner and less rigid and is, thus, easier to insert. Accordingly, devices designed to insert a diaphragm may be designed without the considerations of the strong force required to hold the diaphragm in a folded position, the special folding direction required for insertion (diaphragms may be stretched and bent more readily and their center protective portions more readily adjusted relative to the outer ring) of a pessary 20, and the size limitations required for the more rigid pessary 20.

When folded, the pessary 20 defines a fold 22 and forms a crescent shape. For insertion, the leading edge 24 of the crescent formed by the folded pessary 20 preferably points downward and is, therefore, concave when looked upon by the patient receiving the pessary 20. The distance from the bottom 26 of the fold 22 of the folded pessary 20 to the top 28 of the peripheral edge 30 defines the height of the folded pessary 20. Herein, the relevant height is the height of the portion of the folded pessary 20 held by the body 12.

The side wall portions 16 as measured from the bottom portion 14 of the body 12 have a height that is approximately equal to or greater than the height of the folded pessary 20 in the preferred embodiment. The pessary insertion apparatus 10 is adapted to accommodate various sizes of pessaries 20. The side wall portions 16 may have a height that is slightly greater than the height of the folded pessary 20 and thereby completely encase the pessary 20. Likewise, the pessary 20 may be positioned in the pessary insertion apparatus 10 at a more forward position wherein the portion held in the body 12 is not the portion of the folded pessary 20 having the greatest height. In other words, because the pessary 20 is circular, its greatest height is at the midpoint between the front and back of the folded pessary 20. Therefore, the height of the folded pessary 20 anywhere other than the midpoint is less than the height at the midpoint. Thus, gripping the pessary 20 closer to its back end 32, behind the midpoint, allows the side walls to be less than the height of the folded pessary 20 (as measured at its midpoint) and still reach the upper periphery of the folded pessary 20 with the side wall portions 16. Note however, that the body 12 must engage the pessary 20 relatively near the midpoint in order to ensure a secure hold of the folded pessary 20.

The body 12 is thus adapted and sized to receive and hold a pessary 20 in the folded position therein. When placed in the body 12, the fold 22 of the folded pessary 20 is positioned proximal the bottom portion 14 of the body 12 so that the curve of the body 12 and the curve of the folded pessary 20 curve in the same direction allowing the pessary 20 a closer fit within the body 12 as the curves are approximately parallel. This orientation allows a smaller body 12 fitted to the pessary 20. Additionally, the relative positioning described provides an open top to the pessary insertion apparatus 10 that permits the user an unimpeded view of the pessary 20 from the top while completing the insertion which facilitates ease of insertion.

Additionally, the body 12 is elongated having a length that is sufficient to extend from the vaginal cavity while positioning the pessary 20 in the appropriate place for release into the vaginal cavity. Preferably, the body 12 extends from the vaginal cavity a sufficient distance when so positioned to allow the user to firmly grip the rear end 40 of the pessary insertion apparatus 10. The body 12 is preferably arcuate throughout its full length so that the body 12 holds the vaginal cavity open and the trough 18 defined by the body 12 forms a passageway 42 through which a user may insert his or her finger to easily reach the back of the pessary 20 held in the pessary insertion apparatus 10. The open passageway 42 allows the user to more easily press the pessary 20 from the pessary insertion apparatus 10 into position in the vaginal cavity. Further, the open passageway 42 enhances the comfort of the insertion procedure by providing the hand a defined passageway 42 and eliminating the need for full insertion of the hand.

Figure 3:
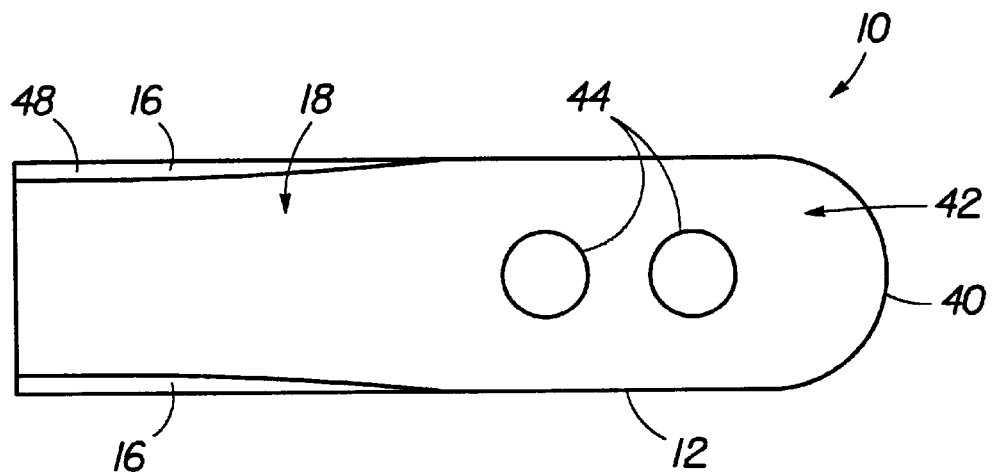
FIG. 3 is a top elevational view of the pessary insertion apparatus.

To further facilitate handling of the pessary insertion apparatus 10 and forcing of the pessary 20 from the pessary insertion apparatus 10, the pessary insertion apparatus 10 also includes means for enhancing the grip on the body 12. FIGS. 1, 2, and 3 show one preferred member to enhance gripping, namely the holes 44 through the bottom portion 14 of the body 12. The holes 44 simply provide a bearing surface against which a user may press with a finger. The pessary insertion apparatus 10 may incorporate one hole 44 or a plurality of holes 44 and the holes 44 may pass fully or partially through the body 12. Similar, alternate embodiments may simply include a roughened portion of the bottom portion 14 that increases the coefficient of friction between the hand and the pessary insertion apparatus 10 and, thus, the grip on the pessary insertion apparatus 10 for the user. A second embodiment of the member to enhance gripping, shown in FIG. 2, is a handle 46 attached to the rear end 40 of the body 12. Although the handle 46 may take many forms, the embodiment shown in the figure is a simple handle 46 that extends downwardly from the rear end 40 of the bottom portion 14 of the body 12. The embodiment shown prevents the rear end 40 of the body 12 from entering the vaginal cavity.

Figure 4:
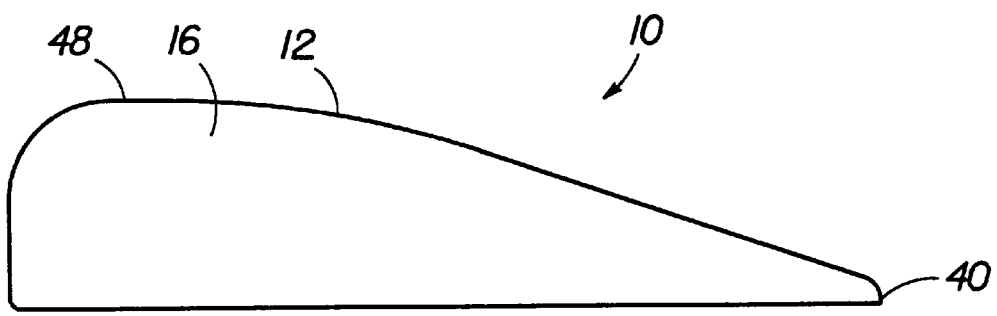
FIG. 4 is a side elevational view of the pessary insertion apparatus.

FIG. 4 is a side elevational view of the pessary insertion apparatus 10. Preferably, the height of the body 12 decreases from its forward end to its rear end 40. The height of the front portion 48 is, as previously discussed, approximately equal to or greater than the height of the folded pessary 20 and is sufficient to receive and hold the folded pessary 20 therein. From the forward portion, the height of the side wall portions 16 decrease toward the rear end 40 to provide for smooth and easy removal of the pessary insertion apparatus 10 from the vaginal cavity. The gradual decrease in height makes sliding of the pessary insertion apparatus 10 from the vaginal cavity more comfortable.

Accordingly, a pessary 20 may be more easily inserted into a vaginal cavity using the pessary insertion apparatus 10 by holding the pessary 20 in a folded position in the front portion 48 of the body 12. The user then inserts the pessary 20, using the pessary insertion apparatus 10, into the vaginal cavity with the leading edge 24 of the crescent formed by the folded pessary 20 pointing downward to a position within the vaginal cavity where the pessary 20 is to be inserted. While holding the vaginal cavity open with the body 12 to define a passageway 42 through which a finger of the user may reach a back end 32 of the pessary 20, the user pushes the pessary 20 from the body 12 of the pessary insertion apparatus 10 into the position within the vaginal cavity where the pessary 20 is to be inserted so that the pessary 20 unfolds. Finally, the user removes the pessary insertion apparatus 10 from the vaginal cavity.

While the foregoing is directed to the preferred embodiment of the present invention, other and further embodiments of the invention may be devised without departing from the basic scope thereof, and the scope thereof is determined by the claims which follow.

I claim:

1. A pessary insertion apparatus for inserting a pessary in a vaginal cavity, comprising:

a substantially rigid body having an arcuate shape defining a bottom portion and a pair of opposing side wall portions and a trough therein;

the body sized and adapted to fit within the vaginal cavity;

the side wall portions extending from the bottom portion a distance approximately equal to or greater than the folded height of the pessary as measured from the bottom of the crescent formed by folding the pessary to the peripheral edge of the portion of the pessary held by and contacting the body; and the body having a u-shape throughout the full length of the body so that the trough is open at its top throughout the full length of the body;

so that the body is sized and adapted to receive and hold a pessary in a folded position.

2. The apparatus of claim 1, wherein:

the body is sized and adapted to receive and hold the pessary in a folded position with the fold formed by the folded pessary proximal the bottom portion of the body; and so that the curve of the body and the curve of the pessary curve in the same direction.

3. The apparatus of claim 1, wherein the body is crescentic.

4. The apparatus of claim 1, wherein the body is elongated.

5. The apparatus of claim 4, wherein:

the body is arcuate throughout its full length; and the trough defines a passageway in the vaginal cavity through which a hand of a user may reach a back end of the pessary;

so that the user may force the pessary from the body into position in the vaginal cavity.

6. The apparatus of claim 1, further comprising means for enhancing the grip on the body.

7. The apparatus of claim 6, wherein the means for enhancing the grip comprises at least one hole defined by the body proximal a rear of the body.

8. The apparatus of claim 7, further comprising a plurality of holes extending through the bottom portion of the body.

9. The apparatus of claim 6, wherein the means for enhancing the grip comprises a handle attached to a rear end of the body.

10. The apparatus of claim 1, wherein the body is formed of a material that may be easily sterilized.

11. The apparatus of claim 10, wherein the body is formed of plastic.

12. The apparatus of claim 10, wherein the body is formed of stainless steel.

13. The apparatus of claim 1, wherein:

the body having a front portion, adapted to receive and hold the pessary therein, and a rear end; and the height of the side wall portions decreasing from the front portion to the rear end; so that the body may be more easily removed from the vaginal cavity.

14. A method of inserting a pessary into a vaginal cavity using a pessary insertion apparatus having a rigid, arcuate body, the body having a u-shape throughout the full length of the body, comprising the steps of:

holding the pessary in a folded position in the front portion of the body, the curve of the folded pessary and the curve of the body curving in the same direction so that the fold created by the folded pessary lies proximal a bottom portion of the body;

inserting the pessary, using the pessary insertion apparatus, into the vaginal cavity with the leading edge of the crescent formed by the folded pessary pointing downward to a position within the vaginal cavity where the pessary is to be inserted;

holding the vaginal cavity open with the body to define a passageway through which a hand of the user may reach a back end of the pessary;

pushing the pessary from the body into the position within the vaginal cavity where the pessary is to be inserted so that the pessary unfolds; and removing the pessary insertion apparatus from the vaginal cavity.

15. The apparatus of claim 1, wherein the body is sized and adapted to hold a rear portion of the pessary so that a front portion of the pessary extends from a front of the body.

* * * * *